US010533981B2

(12) United States Patent
Yi et al.

(10) Patent No.: US 10,533,981 B2
(45) Date of Patent: Jan. 14, 2020

(54) AIR QUALITY MEASUREMENT WITH MODULAR SENSOR SYSTEM AND METHOD

(71) Applicant: The Chinese University of Hong Kong, Shatin, N.T., Hong Kong SAR (CN)

(72) Inventors: Wei-Ying Yi, Foshan (CN); Kwong-Sak Leung, Hong Kong (CN); Yee Leung, Hong Kong (CN)

(73) Assignee: The Chinese University of Hong Kong, Shatin, N.T. (HK)

( * ) Notice: Subject to any disclaimer, the term of this patent is extended or adjusted under 35 U.S.C. 154(b) by 98 days.

(21) Appl. No.: 15/796,244

(22) Filed: Oct. 27, 2017

(65) Prior Publication Data

US 2018/0120279 A1 May 3, 2018

Related U.S. Application Data

(60) Provisional application No. 62/413,854, filed on Oct. 27, 2016.

(51) Int. Cl.
*G01N 33/00* (2006.01)
(52) U.S. Cl.
CPC ..... *G01N 33/0073* (2013.01); *G01N 33/0075* (2013.01)
(58) Field of Classification Search
CPC ........... G01N 33/0073; G01N 33/0063; G01N 33/004; G01N 33/0062; G01N 33/0075; G01N 33/034; G01N 33/00
See application file for complete search history.

(56) References Cited

U.S. PATENT DOCUMENTS 5,255,556 A * 10/1993 Lobdell ............... G01N 1/2273
340/602
6,167,766 B1 * 1/2001 Dunn ...................... G01N 1/18
73/863.01

(Continued)

FOREIGN PATENT DOCUMENTS

| CN | 102665249 A | 9/2012 |
|----|-------------|--------|
| CN | 204302267 U | 4/2015 |

*Primary Examiner* — Helen C Kwok
(74) *Attorney, Agent, or Firm* — Kilpatrick Townsend & Stockton LLP

(57) ABSTRACT

An apparatus for acquiring air quality data from removable and/or replaceable sensor, processing and storing the acquired data, and transmitting the processed data to back-end server is enabled. The apparatus includes a microcontroller coupled with a Universal Sensor Interface (USI). The USI may include an element configured to transmit continuous electrical power to a removable and/or replaceable sensor, an element configured to transmit intermittent electrical power during time intervals corresponding to sensing intervals, an element configured to transmit an indication that the removable and/or replaceable sensor is currently coupled with the sensor interface, and one or more elements configured as a serial peripheral interface. A modular sensor system is thereby enabled, configurable to manage multiple removable and replaceable sensors such as air quality sensors. Distinct interface elements for continuous and intermittent electrical power enable utilization of sensors with relatively long initialization times while optimizing power usage by powering some components only during sensing intervals. Including an interface element indicating presence or absence of the removable and/or replaceable sensor and one or more interface elements configured as a serial peripheral interface with USI protocol enable dynamic plug-and-play reconfiguration of the apparatus.

22 Claims, 13 Drawing Sheets

(56) References Cited

U.S. PATENT DOCUMENTS

| | | | |
|---|---|---|---|
| 9,380,949 B2 * | 7/2016 | Schuessler | A61B 5/02055 |
| 9,800,646 B1 * | 10/2017 | Stamatakis | H04L 67/025 |
| 10,178,638 B1 * | 1/2019 | Stamatakis | H04W 56/002 |
| 2006/0173579 A1 * | 8/2006 | Desrochers | G01N 1/26 |
| | | | 700/276 |
| 2011/0276738 A1 | 11/2011 | Kim et al. | |
| 2013/0007316 A1 | 1/2013 | Moon et al. | |
| 2014/0053586 A1 * | 2/2014 | Poecher | G01D 1/18 |
| | | | 62/126 |
| 2015/0185161 A1 * | 7/2015 | Gettings | G01N 21/84 |
| | | | 73/865.8 |
| 2015/0212057 A1 * | 7/2015 | Darveau | G01N 33/004 |
| | | | 73/31.03 |
| 2015/0268205 A1 * | 9/2015 | Gettings | G01N 33/00 |
| | | | 73/865.8 |
| 2016/0146769 A1 * | 5/2016 | Zhang | G01N 33/0063 |
| | | | 73/31.02 |

\* cited by examiner

AIR QUALITY MEASUREMENT WITH MODULAR SENSOR SYSTEM AND METHOD

FIELD OF THE INVENTION

This invention pertains generally to measurement of environmental attributes and, more particularly, to measurement of environmental attributes with electronic sensors.

BACKGROUND

Air pollution attracts extensive attention globally due to its critical impacts on human health, the environment and the economy. Monitoring systems providing real-time micro-level pollution information have been developed to provide authorities with data to mitigate these impacts. However, conventional systems are usually application-specific with fixed hardware and software configurations. They can be inconvenient to maintain, difficult to reconfigure, and/or insufficiently expandable with respect to sensing capabilities. In addition, conventional system can have low spatial and temporal resolutions and be inadequate for monitoring personal and acute exposures to air pollutants.

Embodiments of the invention are directed toward solving these and other problems individually and collectively.

BRIEF SUMMARY

In accordance with at least one embodiment of the invention, an apparatus for air quality measurement is enabled. The apparatus may include a microcontroller coupled with a sensor interface (at times herein called a "Universal Sensor Interface" or USI). The sensor interface may include an electronic coupler configured to transmit continuous electrical power to a removable and/or replaceable sensor, an electronic coupler configured to transmit intermittent electrical power during time intervals corresponding to sensing intervals, an electronic coupler configured to transmit an indication that the removable and/or replaceable sensor is currently coupled with the sensor interface, and one or more electronic couplers configured as a serial peripheral interface. At least in part by establishing such a standardized sensor interface, a modular sensor system may be enabled, configurable to manage multiple removable and/or replaceable sensors such as air quality sensors. The apparatus may include any suitable number of such sensor interfaces, each accommodating a different removable and/or replaceable sensor (supporting sensor with multiple environmental attributes outputs). In accordance with at least one embodiment of the invention, distinct interface elements for continuous and intermittent electrical power enables utilization of sensors with relatively long initialization times while optimizing (e.g., minimizing) power use by powering some components only during sensing intervals. In accordance with at least one embodiment of the invention, including an interface element indicating presence or absence of the removable and/or replaceable sensor enables dynamic "plug-and-play" reconfiguration of the apparatus to utilize new removable and/or replaceable sensors.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

BRIEF DESCRIPTION OF THE DRAWINGS

Illustrative embodiments of the present invention are described in detail below with reference to the following drawing figures.

Note that the same numbers are used throughout the disclosure and figures to reference like components and features.

DETAILED DESCRIPTION

Figure 1:
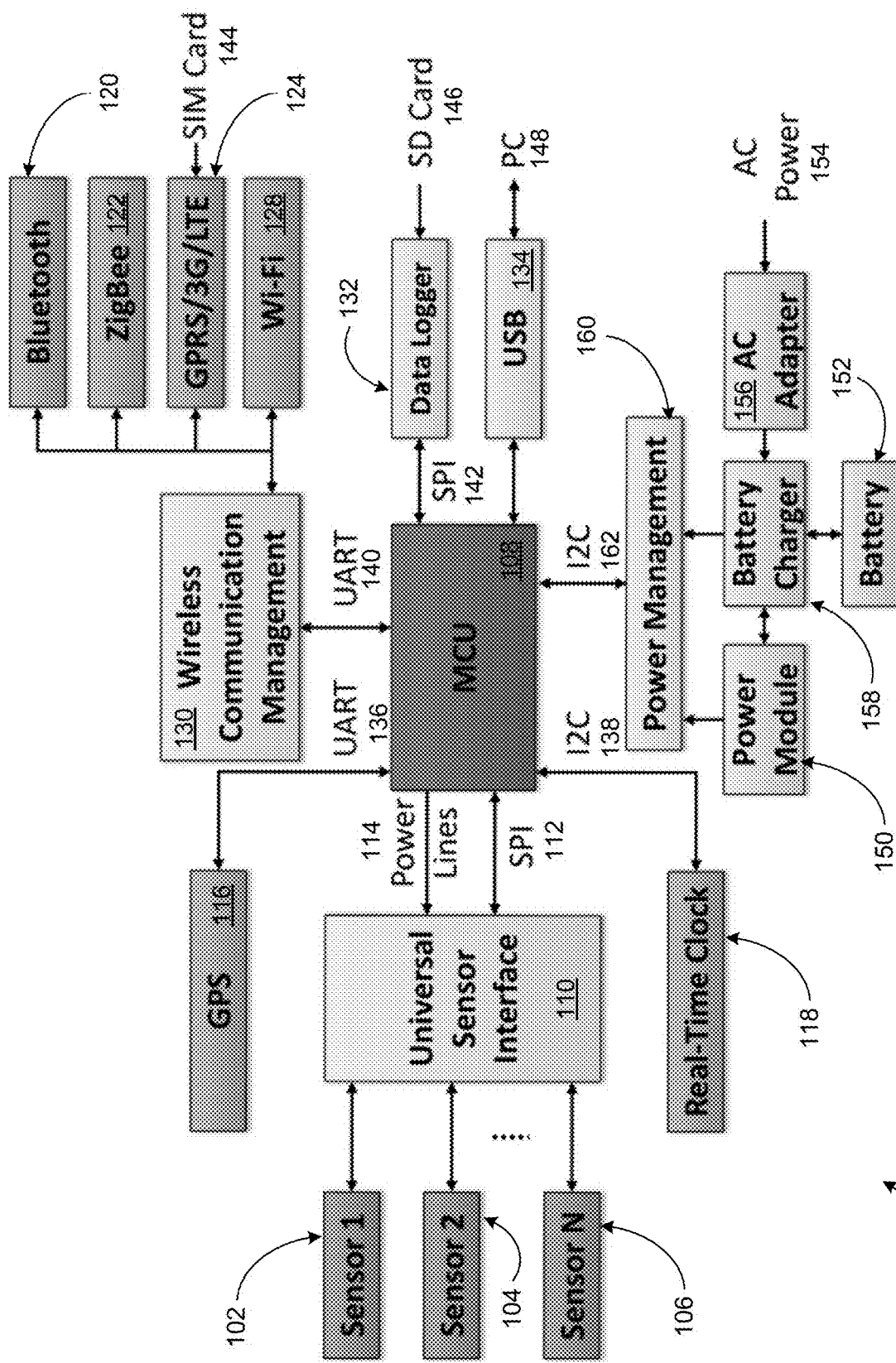
FIG. 1 is a schematic diagram depicting aspects of example system architecture in accordance with at least one embodiment of the invention.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

In accordance with at least one embodiment of the invention, an apparatus for air quality measurement is enabled. The apparatus may include a microcontroller coupled with a sensor interface (at times herein called a "Universal Sensor Interface" or USI). The sensor interface may include an electronic coupler configured to transmit continuous electrical power to a removable and/or replaceable sensor, an electronic coupler configured to transmit intermittent electrical power during time intervals corresponding to sensing intervals, an electronic coupler configured to transmit an indication that the removable and/or replaceable sensor is currently coupled with the sensor interface, and one or more electronic couplers configured as a serial peripheral interface. At least in part by establishing such a standardized sensor interface, a modular sensor system may be enabled, configurable to manage multiple removable and/or replaceable sensors such as air quality sensors. The apparatus may include any suitable number of such sensor interfaces, each accommodating a different removable and/or replaceable sensor (supporting sensor with multiple environmental attributes outputs). In accordance with at least one embodiment of the invention, distinct interface elements for continuous and intermittent electrical power enables utilization of sensors with relatively long initialization times while optimizing (e.g., minimizing) power use by powering some components only during sensing intervals. In accordance with at least one embodiment of the invention, including an interface element indicating presence or absence of the removable and/or replaceable sensor enables dynamic "plug-and-play" reconfiguration of the apparatus to utilize new removable and/or replaceable sensors. As used herein, the term "removable sensor" includes sensors capable of being removably attached with the sensor interface of the apparatus. As used herein, the term "replaceable sensor" includes sensors attached with the apparatus (e.g., via the sensor interface) that are capable of being replaced with different sensors.

In accordance with at least one embodiment of the invention, a Modular Sensor System (MSS) is enabled, which addresses shortcomings of existing wireless sensor network (WSN) based monitoring systems and methods at least in part by adopting a Universal Sensor Interface (USI) and a modular design in a sensor node. A compact MSS sensor node with expandable plug-and-play sensor modules and compatibility with multiple types of wireless sensor networks (WSNs) is enabled. MSS sensor nodes can be deployed in different scenarios while dynamically adapting to reconfigurations and monitoring air pollution at low concentration levels with high energy efficiency. The MSS is able to ease efforts with respect to system maintenance, adaptation, and evolution in real-life large-scale deployment situations.

In accordance with at least one embodiment of the invention, configurable sensing capability is enabled (e.g., number of sensor modules, types of sensor modules, and sensing rates of sensor modules are configurable based on the application). In addition, multiple types of WSNs may be compatibility supported (e.g., type of the wireless communication module is carefully selected based on the deployment scenario to ensure the network-connectivity and cost-efficiency). In addition, a reconfiguration adaptability is enabled. In accordance with at least one embodiment of the invention, sensor modules inserted are able to be automatically identified and suitable handling schema may be selected (sometimes called "plug-and-play" capability).

In accordance with at least one embodiment of the invention, real-time air pollution information with high spatiotemporal resolution and in-time personal acute exposure warnings are enabled by deploying large numbers of stationary, wearable, or vehicular sensor nodes in the field. Systems in accordance with at least one embodiment of the invention may include:

A Modular Sensor System (MSS) architecture with configurable sensing capability, multiple WSNs compatibility, and reconfiguration adaptability;

A Universal Sensor Interface (USI) enabling modular design in hardware/software, energy efficiency, configurable sensing capability, and reconfiguration adaptability; and A compact MSS sensor node with multiple (e.g., six) plug-and-play sensor modules and multiple WSNs compatibility, which is easy to use and maintain, and can be conveniently reconfigured for different monitoring scenarios.

An example system architecture of an MSS 100 in accordance with at least one embodiment of the invention is illustrated in FIG. 1. Each sensor 102, 104, 106 is connected with the microcontroller (MCU) 108 through the Universal Sensor Interface (USI) 110. Multiple sensors on-board ability, configurable sensing capability, and dynamic reconfiguration adaptability may be enabled by the USI 110. As indicated by the ellipsis, any suitable number of sensors may be communicatively connected with the MCU 108. Also, a low-footprint Serial Peripheral Interface (SPI) 112 based protocol, enabling dynamic reconfiguration adaptability, is adopted for communication between the sensors 102, 104, 106 and the MCU 108. Power lines 114 of sensors may be controlled by the MCU 108 for power management, detection maximizing, and fault tolerance purposes.

A global positioning system (GPS) module 116 and a real-time clock module 118 may be utilized to tag location (including current geographical location) and time information (including current date and/or time) to sensing data, respectively. The GPS module 116 may be communicatively connected with the MCU 108 utilizing a universal asynchronous receiver-transmitter (UART) port 136 of the MCU 108. The real-time clock module 118 may be communicatively connected with the MCU 108 utilizing an Inter-Integrated Circuit (I2C) bus 138. Multiple wireless sensor network (WSN) modules (e.g., Bluetooth 120, ZigBee 122, GPRS/3G/LTE 124, Wi-Fi 128) may be supported by a wireless communication management module 130, which ensures the network-connectivity and power-efficiency of sensor nodes in different kinds (stationary, wearable, or vehicular) of deployment scenarios. The wireless communication management module 130 may be communicatively connected with the MCU 108 utilizing a UART port 140 of the MCU 108. One or more of the WSN modules 120, 122, 124, 128 may be communicatively connected with (e.g., removably connected with) one or more additional components and/or devices that enable wireless communication. For example, the GPRS/3G/LTE module 124 may be associated with a subscriber identification module (SIM) card 144. A data logger 132, a universal serial bus (USB) 134, and a battery power system may be utilized for data recording, debugging, and power management purposes respectively. The data logger 132 may be communicatively connected with the MCU 108 utilizing an SPI port 142 of the MCU 108. The data logger 132 may be communicatively connected with (e.g., removably connected with) one or more additional components and/or devices that store data logged by the data logger 132. For example, the data logger 132 may be communicatively connected with a secure digital non-volatile memory (SD) card 146. The USB may communicatively connect the MCU 108 with one or more additional peripherals and/or computing devices such as a personal computer (PC) 148.

The battery power system may include a power module 150 that supplies electrical power to any suitable component of the MSS 100. The power module may be electrically coupled with a battery 152 and/or an alternating current (AC) power supply 154. The power module 105 may receive the AC power 154 by way of an AC adapter 156 that converts the AC power to DC power. The AC adapter 156 may be additionally coupled with a battery charger 158 capable of charging the battery 152 utilizing the converted AC power 154. The battery charger 158 may electrically couple the power module 150 with the battery 152 and/or the AC adapter 156. The power module 150 and/or the battery charger 158 may provide information to and be controlled by a power management module 160. The power management module 160 may be communicatively coupled with the MCU 108 utilizing an I2C bus 162. The MCU 108 may receive information from and issue commands to the power management module 160 to optimize MSS 100 power utilization and/or any suitable power-related operational parameter.

Figure 2:
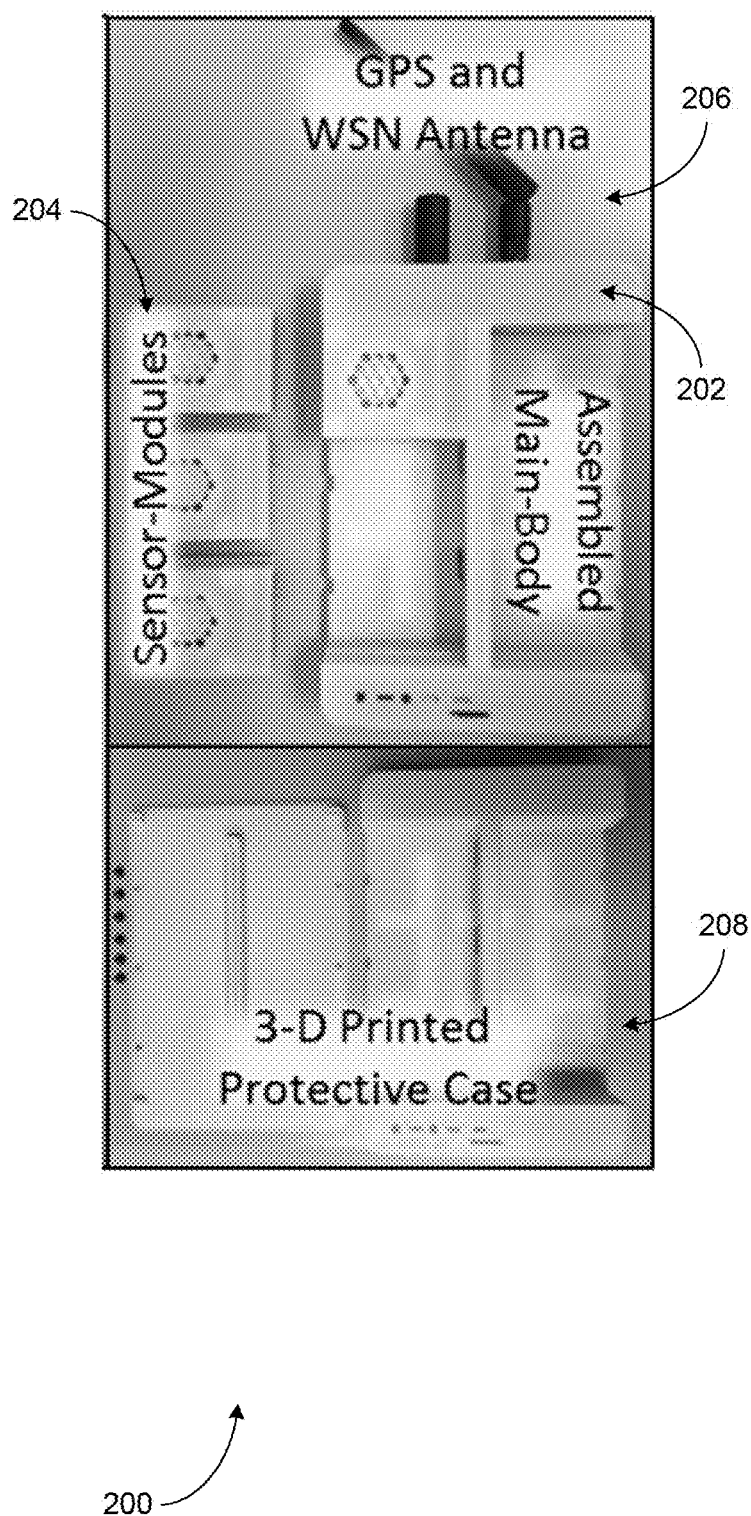
FIG. 2 depicts aspects of example multi-sensor platform hardware in accordance with at least one embodiment of the invention.

FIG. 2 depicts aspects of sensor node 200 hardware in accordance with the MSS architecture 100 (FIG. 1). The sensor node 200 may be decomposed into two subsystems, namely a Main-Body 202 and one or more Sensor-Modules 204. The Main-Body 202 may incorporate a sensor management module (not shown in FIG. 2) that manages the one or more Sensor-Modules 204. For example, the sensor management module may enable and/or facilitate Main-Body functionality with respect to the Sensor-Modules 204 as described below. At times, the term "sensor management module" is used interchangeably with the term "Main-Body." In the example depicted in FIG. 2, one Sensor-Module 204 is removably attached with the Main-Body 202 and there is space for five (5) more Sensor-Modules 204. Three (3) Sensor-Modules 204 are shown unattached beside the Main-Body 202. The Main-Body 202 is also shown attached with GPS and WSN antennas 206. Further aspects of the protective case 208 are shown. For example, the protective case 208 may be printed with a 3D printer. As one example, the Main-Body 202 may have approximate dimensions of 180 mm long by 123 mm wide by 36 mm high (without antennas) and weigh approximately 320 grams. As one example, the Sensor-Module 204 may have approximate dimensions 56 mm long by 44 mm wide by 26 mm high and weigh between 38 and 45 grams each. However Sensor-Module parameters may vary. For example, the first example dimensions and weights may correspond to sensors for $CO_2$, CO, $SO_2$, $O_3$, $NO_2$, temperature, relative humidity, air pressure, $\beta$ radiation and/or $\gamma$ radiation. At times, such a sensor may be capable of detecting multiple parameters, for example, a single sensor of such dimensions may detect temperature, relative humidity and air pressure, or $\beta$ radiation and $\gamma$ radiation. As another example, a sensor capable of detecting radiation $\beta$ radiation, $\gamma$ radiation, as well as $\alpha$ radiation may have approximate dimensions of 88 mm long by 56 mm wide by 36 mm high and weigh 150 grams. As yet another example, a particulate matter (PM) sensor capable of detecting PM1, PM2.5 and PM10 may have approximate dimensions 88 mm long by 56 mm wide by 65.5 mm high and weigh approximately 130 grams. For example, these last two examples may occupy two Sensor-Module accommodations on the Main-Body.

Figure 3:
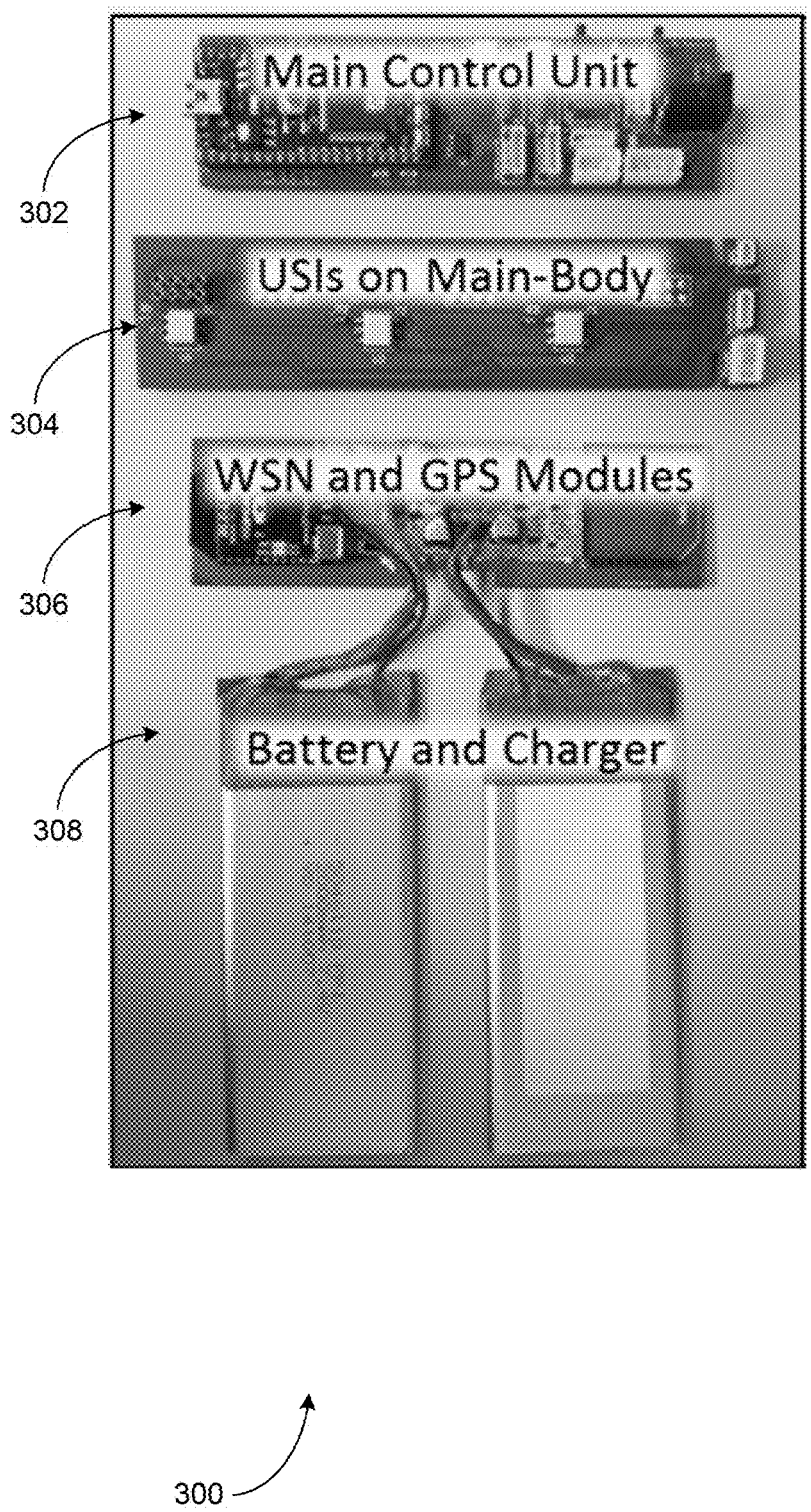
FIG. 3 depicts aspects of example multi-sensor platform hardware in accordance with at least one embodiment of the invention.

FIG. 3 depicts aspects of Main-Body 202 (FIG. 2) hardware 300 in accordance with the MSS architecture 100 (FIG. 1). For example, the hardware 300 may be installed inside the protective case 208. The hardware 300 may include a circuit board 304 configured to provide multiple (e.g., six) USIs, a circuit board 302 configured to provide a main control unit, and a circuit board 306 configured to provide a WSN and a GPS module. Rechargeable batteries 308 may be configured to incorporate charging and power management circuitry. Alternatively, or in addition, charging and/or power management circuitry may be incorporated into one or more of the circuit boards 302, 304, 206. Although the example in FIG. 3 depicts support for six (6) Sensor-Modules, in accordance with at least one embodiment of the invention, the Main-Body may be configured to support sixteen (16) or more Sensor-Modules.

Figure 4:
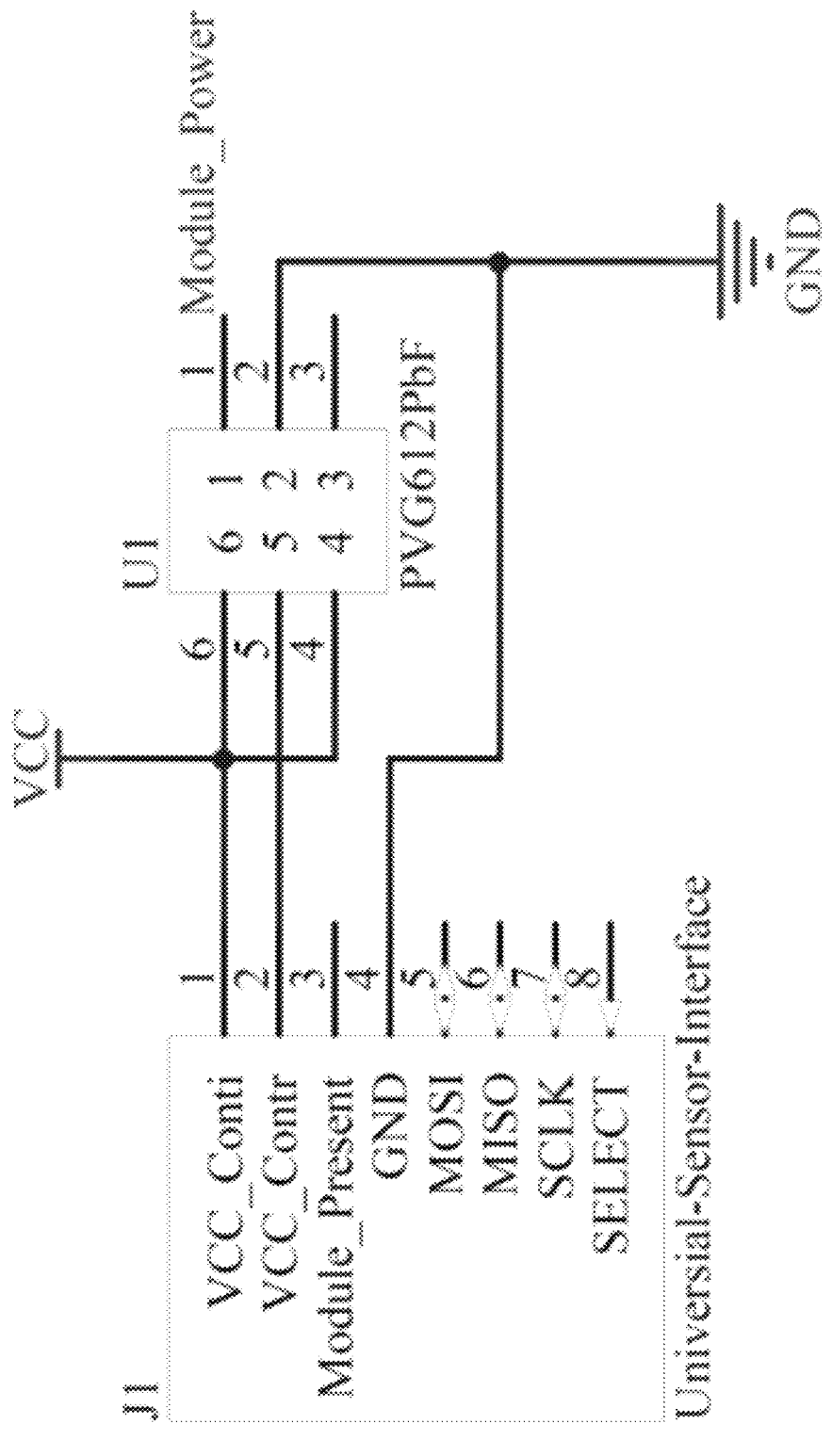
FIG. 4 is a schematic diagram depicting aspects of an example sensor interface in accordance with at least one embodiment of the invention.

Aspects of an example USI 400 on a Main-Body is shown in FIG. 4. Connector J1 is the 8-pin connector of USI. Pin VCC_Conti provides power for components in Sensor-Module 204 (FIG. 2) that require continual power. Controlled by main control unit 108 (FIG. 1) using signal Module_Power on relay U1, Pin VCC_Contr provides power for the module control unit in the Sensor-Module 204.

The signal on pin Module_Present is driven low to notify the main control unit 108 (FIG. 1) whenever a Sensor-Module 204 (FIG. 2) is inserted into the Main-Body 202, enabling the configurable sensing capability and dynamic reconfiguration adaptability. MOSI, MISO, SCLK, and SELECT are standard pins for SPI communication. A low-footprint SPI based communication protocol between Main-Body and Sensor-Module is implemented and an example timing diagram is presented in FIG. 5. An MCU (e.g., an Mbed LPC1768), a real-time clock (RTC) integrated circuit (IC), and a nonvolatile memory card (e.g., MicroSD) based data logger are utilized in the Main-Body 202. Multiple sensors are supported by using multiple IO expanders (e.g., three 16-bit IO expanders) to control signals Module_Power, SELECT, and Module_Present on USIs respectively. In accordance with at least one embodiment of the invention, an Xbee footprint is adopted, in which case any suitable Xbee packaged WSN modules can be incorporated in the Main-Body 202.

Figure 5:
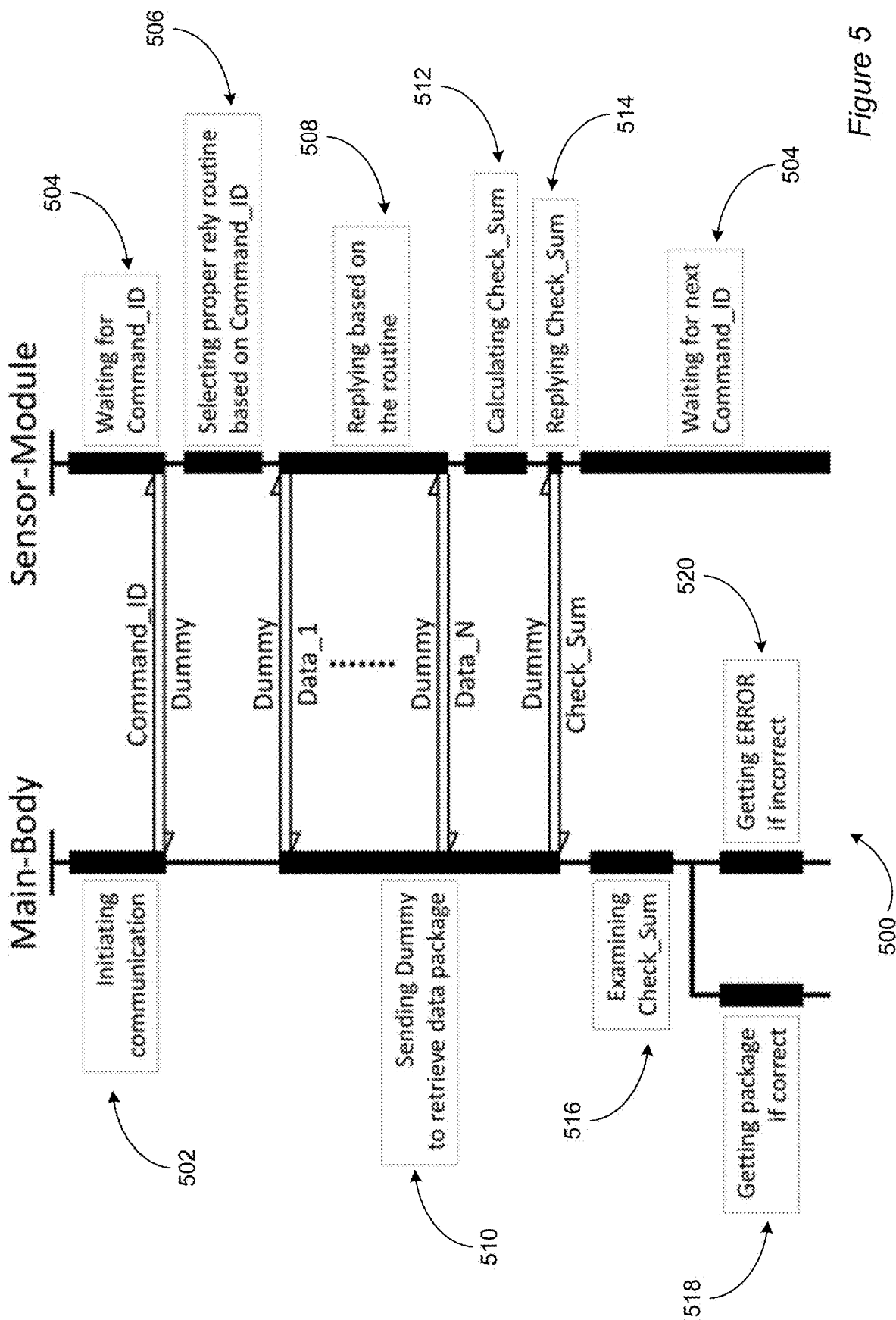
FIG. 5 is a schematic diagram depicting aspects of an example communication protocol in accordance with at least one embodiment of the invention.

FIG. 5 depicts aspects of an example communication protocol 500 between a Main-Body 202 (FIG. 2) and a Sensor-Module 204 utilizing SPI 112 (FIG. 1) in accordance with at least one embodiment of the invention. In an initiating communication phase 502, the Main-Body sends a Command_ID message to the Sensor-Module, which is in a waiting for Command_ID phase 504. The Sensor-Module replies with a Dummy message (e.g., an SPI compliant byte or block with all bits sets to zero). The Sensor-Module may then progress to a Selecting proper reply routine phase 506. In phase 506, a suitable reply routine may be selected based on the unique Command_ID in the received Command_ID message, and the Sensor-Module may progress to a replying based on the selected routine phase 508. With reference to FIG. 5, the terms "phase" and "state" can be used interchangeable unless indicated otherwise and/or as is clear from the context.

Responsive to receiving the Dummy message from the Sensor-Module, the Main-Body may progress to a retrieve data package phase 510. During phase 510, the Main-Body may send Dummy messages to retrieve an N-segment data message and a transmission error detecting message (e.g., Check_Sum message) from the Sensor-Module. For example, the Main-Body may send N+1 Dummy messages. The Sensor-Module may reply to each of the first N Dummy message with one segment of the N-segment data message (e.g., segment Data_1 through Data_N), and to the last Dummy message with a Check_Sum message calculated during a calculating Check_Sum phase 512. The Check_Sum message containing a checksum for the data sent in the N-segment data message may be sent from the Sensor-Module during a Replying Check_Sum phase 514. The Sensor-Module may then progress to a Waiting for Command_ID phase 504. The Command_ID message may indicate and/or determine the number of segments of the N-segment data message to send. Alternatively, or in addition, the Command_ID message may indicate to send a suitable and/or sufficient amount of segments of the N-segment data messages (including enough segments of the N-segment data message to communicate all unsent sensor data). Receipt of the Check_Sum message (as distinct from an N-segment data message) may indicate to the Main-Body that no further segment of the N-segment data message will be sent from the Sensor-Module in response to Dummy messages.

Responsive to receiving the Check_Sum message from the Sensor-Module, the Main-Body may progress to an examining Check_Sum phase 516. During phase 516, the Main-Body may determine if the received checksum matches a checksum calculated by the Main-Body for the data received in the N-segment data message. If the checksum matches, the Main-Body may progress to a getting package phase 518 in which the N-segment data message is considered to have been successfully transmitted to the Main-Body. Otherwise, the Main-Body may progress to an error phase 520 in which the N-segment data message is considered to have been corrupted during transmission. The Main-Body may take any suitable action during the error phase 520 including requesting retransmission if possible and/or indicating or discarding the N-segment data message as corrupted.

Figure 6:
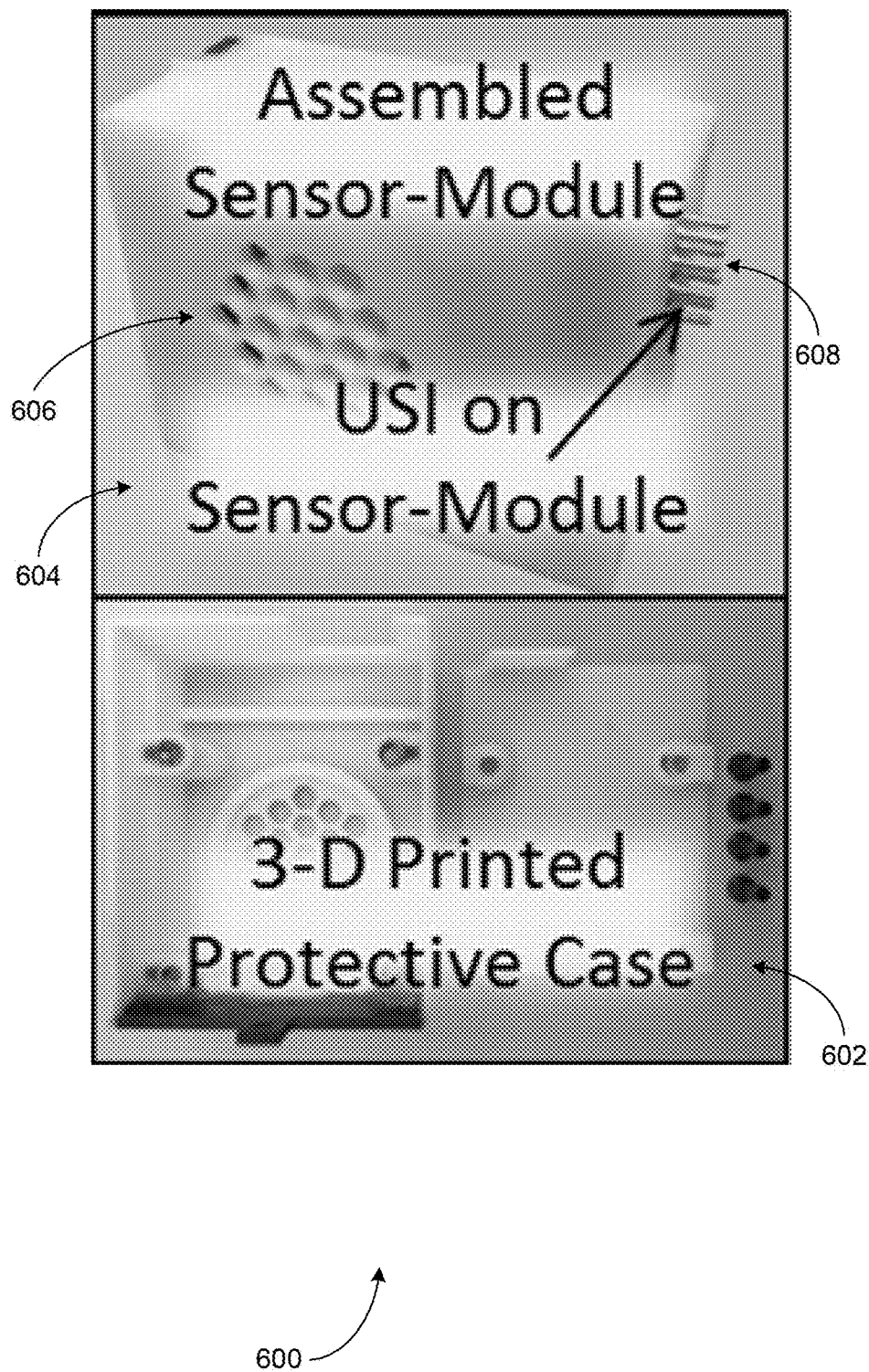
FIG. 6 depicts aspects of example sensor components in accordance with at least one embodiment of the invention.

FIG. 6 depicts aspects of example sensor hardware 600 in accordance with at least one embodiment of the invention. In this example, the sensor hardware 600 is for a carbon monoxide (CO) Sensor-Module. In accordance with at least one embodiment of the invention, enabled at least in part by the USI and the low-footprint SPI based protocol, any suitable sensors satisfying the resource constraints (size, weight, power, etc.) can be configured for inclusion in the MSS 100 (FIG. 1). The sensor hardware 600 includes a protective case 602. For example, the protective case 602 may be printed with a 3D printer. When assembled, the Sensor-Module 604 has an environmental interface 606 (e.g., a sensitive and/or porous surface or aperture array configured to allow gas and/or radiation exchange between the environment and the interior of the protective case 602) and a USI 608. The environmental interface 606 may vary in appearance based on the type of sensor. The USI 608 is configured to be physically compatible the USI 304 (FIG. 3) on the Main-Body (e.g., to physically compliment, be "male" where the Main-Body USI is "female," etc) to provide for removable attachment of the Sensor-Module with the Main-Body. Although not shown in FIG. 6, the Sensor-Module 604 may also incorporate one or more visual and/or audible indicators (e.g., LEDs, buzzers, etc) configure to indicate status with respect to power, operation and/or environment parameters including environmental parameter level warnings (e.g., excessive toxic gas or radiation levels).

Figure 7:
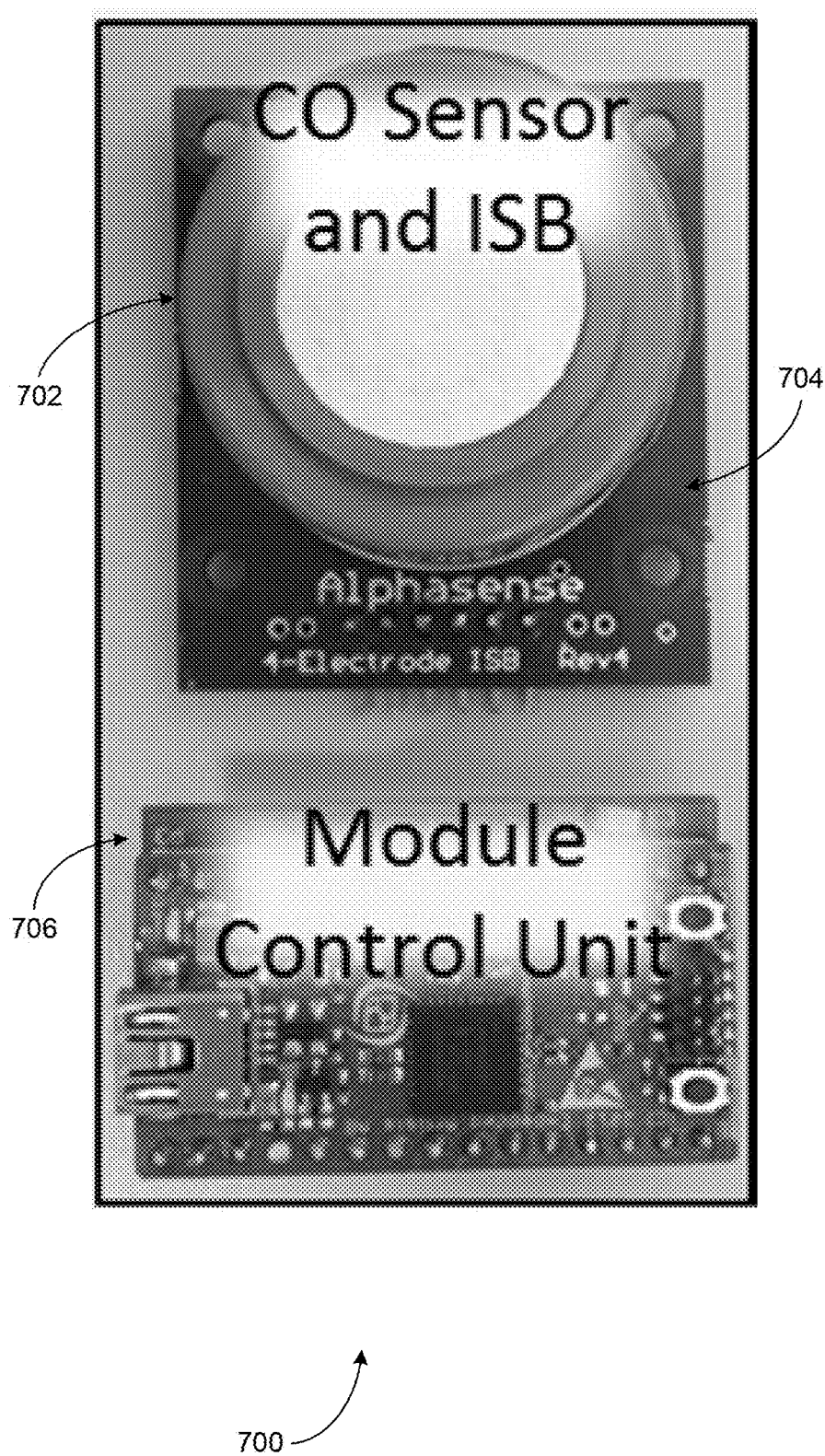
FIG. 7 depicts aspects of example sensor components in accordance with at least one embodiment of the invention.

FIG. 7 depicts further aspects of example sensor hardware 700 in accordance with at least one embodiment of the invention. For example, an Alphasense B4 series electrochemical CO sensor 702 and its supporting circuit or individual sensor board (ISB) 704 may be selected because they can measure CO with ppb-level resolution and mW-level power consumption. The CO sensor and ISB are powered by VCC_Conti (FIG. 4) continuously and the module control unit 706 (e.g., Mbed LPC11U35 MCU and/or other suitable devices) is powered by VCC_Contr in every sensing interval, which need not be continuous. For example, sensing intervals may be determined by the MCU 108 (FIG. 1). Such mechanism can ensure high energy efficiency and good data quality simultaneously because some sensors require an initialization and/or stabilization time (e.g., 2 hours) every time after switching on.

Figure 8:
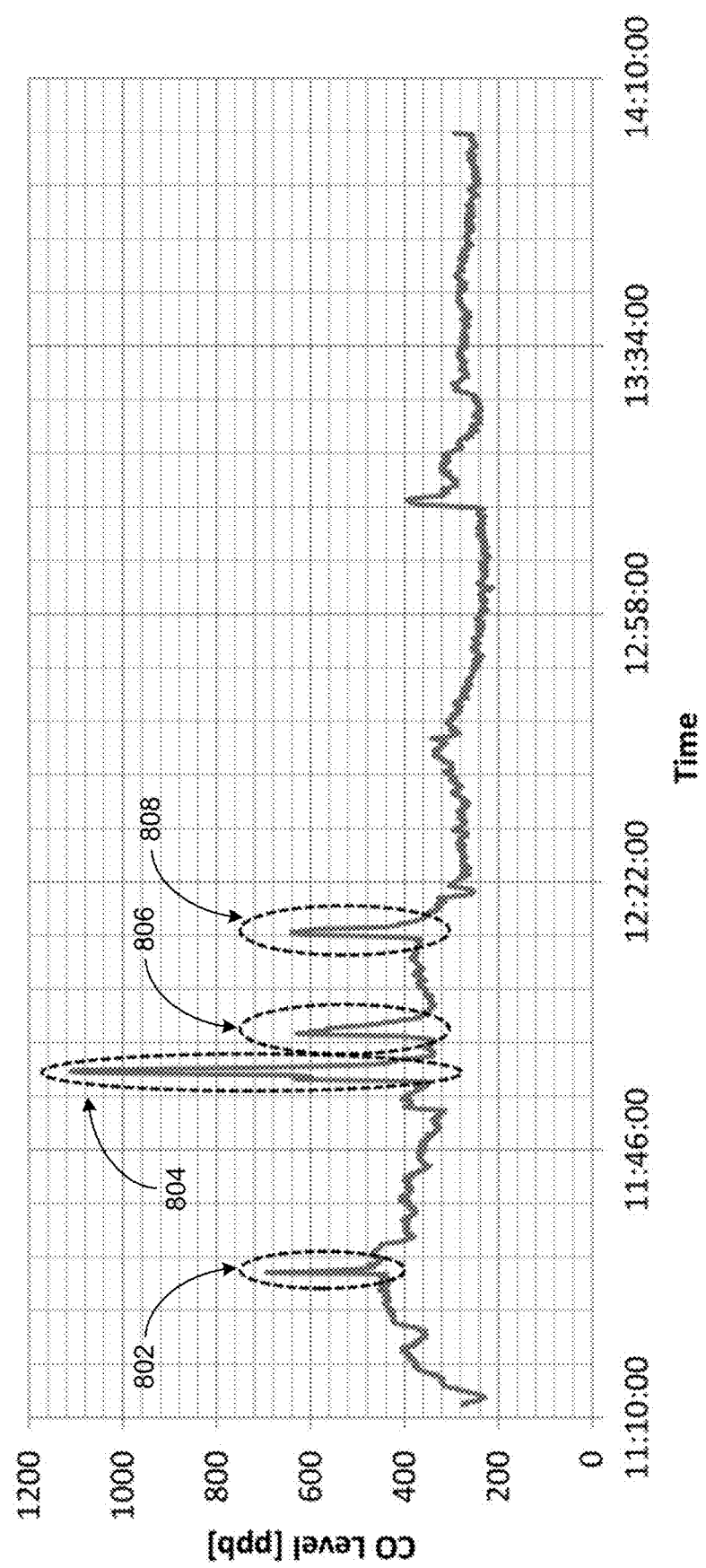
FIG. 8 is a graph depicting aspects of example sensor data in accordance with at least one embodiment of the invention.
Figure 9:
FIG. 9 is a screen shot depicting aspects of an example graphical user interface in accordance with at least one embodiment of the invention.
Figure 10:
FIG. 10 is a screen shot depicting aspects of an example graphical user interface in accordance with at least one embodiment of the invention.
Figure 11:
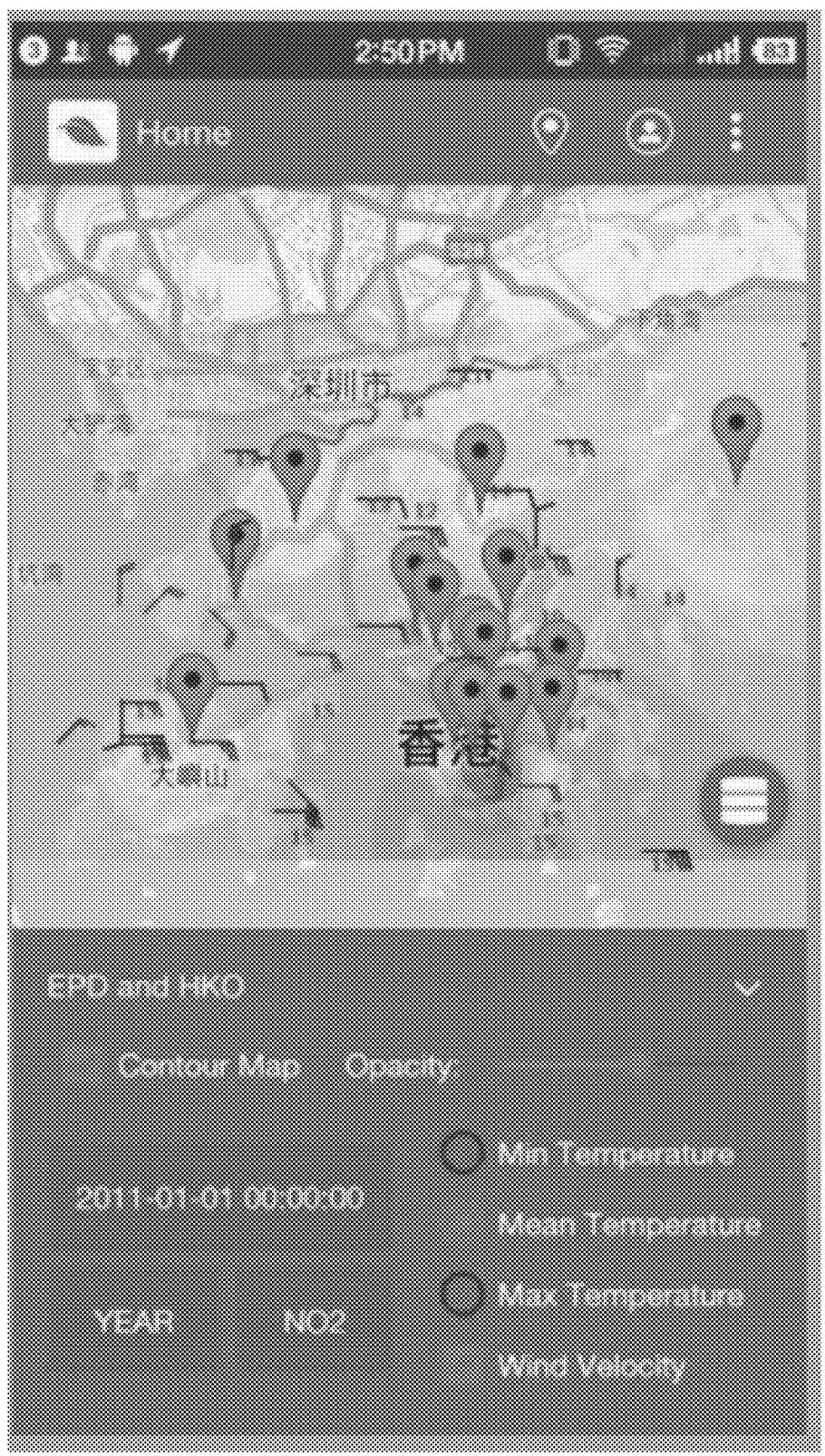
FIG. 11 is a screen shot depicting aspects of an example graphical user interface in accordance with at least one embodiment of the invention.
Figure 12:
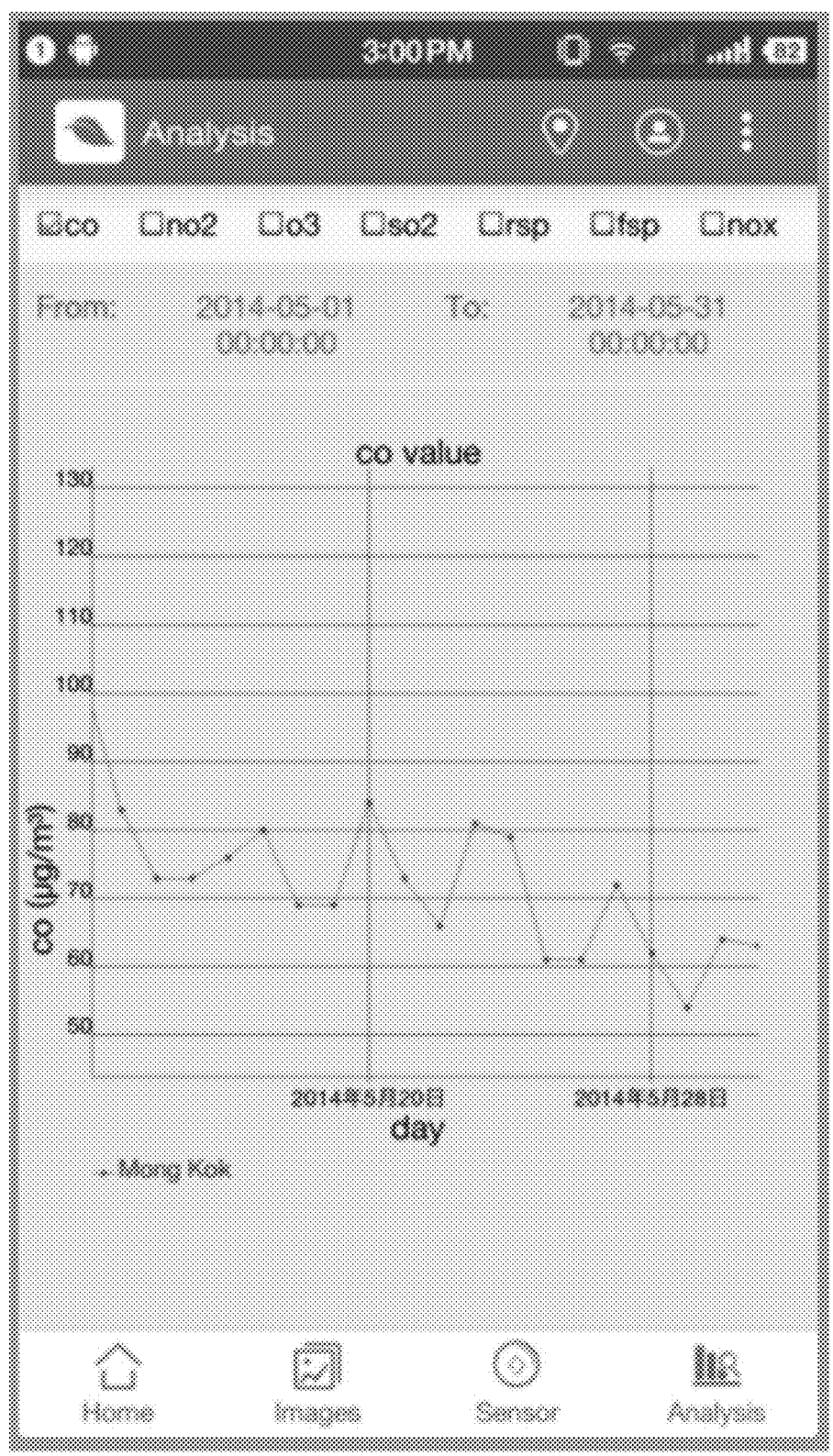
FIG. 12 is a screen shot depicting aspects of an example graphical user interface in accordance with at least one embodiment of the invention.

The Main-Body 202 (FIG. 2) of the MSS sensor node 200 hardware adopting the MSS architecture 100 (FIG. 1) may be connected to a PC 148 through USB 134 for data collection. FIG. 8 depicts example data collected by the MSS sensor node 200 as a graph 800 of carbon monoxide (CO) concentration over time. Main-Body 202 may successfully identify the Sensor-Module 204 inserted and may select a suitable data handling schema (e.g., data retrieval routine, sampling schedule, sampling rate, etc). In this example, the data acquisition rate is one sample every 5 seconds and the sensor node 200 was placed next to a road through a university campus. The first four peaks 802, 804, 806, 808 were recorded right after campus shuttle buses passed by the MSS sensor node 200. This illustrates real-time, low-concentration air pollution information being captured by the sensor node 200 adopting the MSS architecture 100, enabling in-time personal exposure warnings.

A smartphone app (e.g., an Android App) may be implemented for receiving data from the MSS sensor node 200 (FIG. 2) hardware adopting the MSS architecture 100 (FIG. 1) through a wireless communication connection (e.g., Bluetooth) and latter transmitting the data to a data sink (e.g., through a cellular network or Wi-Fi). Example screen shots of an app are shown in FIGS. 9-12. Screen 900 may present sensor data from the Sensor-Modules 204 mounted on the Main-Body 202 including wireless communication connection (e.g., Bluetooth) status such as connected or disconnected, and sensor readings corresponding to environmental gases (e.g., CO, $SO_2$, $NO_2$, $O_3$) including date, time and location of the readings. Screen 1000 may present sensor data (e.g., CO, $SO_2$, $NO_2$, $O_3$, $PM_{10}$, $PM_{2.5}$) from multiple monitoring stations of a government agency (e.g., Environmental Protection Department of Hong Kong) in the context of geographical indications such as a map. Selecting a geographical location associated with a station (e.g., Mong Kok station) may cause pollution data to be displayed including date and time of last update. Screen 1100 may present sensor data (e.g., temperature, wind velocity and direction, $NO_2$) from multiple monitoring stations of government agency (e.g., Environmental Protection Department of Hong Kong and/or Hong Kong Observatory) in the context of geographical indications such as a map as well as additional contextual data such as elevation (e.g., a geographical contour overlay). The additional contextual data may be selectable and/or configurable including with respect to presentation (e.g., configurable opacity for overlay data). Screen 1200 may present sensor data (e.g., CO, $SO_2$, $NO_2$, $O_3$, RSP, FSP, $NO_x$) from a selected monitoring station of a government agency (e.g., Environmental Protection Department of Hong Kong) with respect to time, e.g., historical data including changes over time. Any suitable presentation format may be utilized including data value vs. time graphs.

Figure 13:
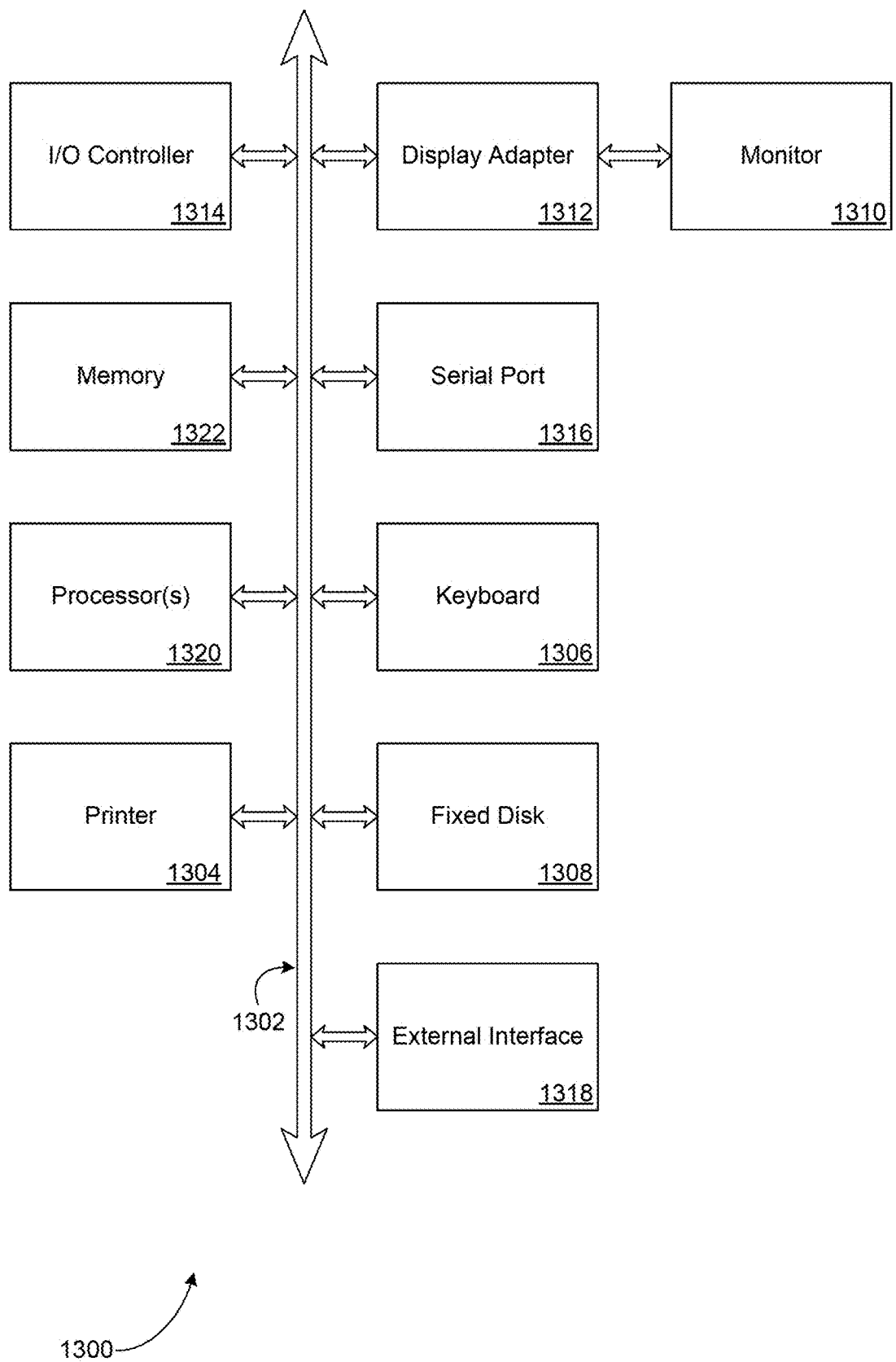
FIG. 13 is a schematic diagram depicting aspects of an example computing device in accordance with some embodiments of the present invention.

In accordance with at least some embodiments, one or more aspects of systems, apparatus, methods, processes and/or operations for air quality measurement may be at least partially implemented in the form of a set of instructions executed by one or more programmed computer processors such as a central processing unit (CPU) or microprocessor. Such processors may be incorporated in an apparatus, server, client, smart phone or other computing device operated by, or in communication with, other system components. As an example, FIG. 13 depicts aspects of elements that may be present in a computer device and/or system 1300 in accordance with some embodiments of the present invention. The subsystems shown in FIG. 13 are interconnected via a system bus 1302. Additional subsystems such as a printer 1304, a keyboard 1306, a fixed disk 1308, a monitor 1310, which is coupled to a display adapter 1312. Peripherals and input/output (I/O) devices, which couple to an I/O controller 1314, can be connected to the computer system by any number of means known in the art, such as a serial port 1316. For example, the serial port 1316 or an external interface 1318 can be utilized to connect the computer device 1300 to further devices and/or systems not shown in FIG. 13 including a wide area network such as the Internet, a mouse input device, and/or a scanner. The interconnection via the system bus 1302 allows one or more processors 1320 to communicate with each subsystem and to control the execution of instructions that may be stored in a system memory 1322 and/or the fixed disk 1308, as well as the exchange of information between subsystems. The system memory 1322 and/or the fixed disk 1308 may embody a tangible computer-readable medium.

It should be understood that the present invention as described above can be implemented in the form of control logic using computer software in a modular or integrated manner. Alternatively, or in addition, embodiments of the invention may be implemented partially or entirely in hardware, for example, with one or more circuits such as electronic circuits, optical circuits, analog circuits, digital circuits, integrated circuits ("IC", sometimes called a "chip") including application-specific ICs ("ASICs") and field-programmable gate arrays ("FPGAs"), and suitable combinations thereof. In particular, the system architecture describe above with reference to FIG. 1 may be partially or entirely implemented in hardware. As will be apparent to one of skill in the art, notions of computational complexity and computational efficiency may be applied mutatis mutandis to circuits and/or circuitry that implement computations and/or algorithms. Based on the disclosure and teachings provided herein, a person of ordinary skill in the art will know and appreciate other ways and/or methods to implement the present invention using hardware and/or a combination of hardware and software.

Any of the software components, processes or functions described in this application may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

Example embodiments in accordance with the invention are described below.

Example 1 is an apparatus for air quality measurement, the apparatus comprising: a microcontroller; a sensor interface electrically coupled with the microcontroller, the sensor interface comprising: a first electronic coupler configured to transmit continuous electrical power to a removable sensor; a second electronic coupler configured to transmit intermittent electrical power during time intervals corresponding to sensing intervals determined by the microcontroller; a third electronic coupler configured to transmit an indication that the removable sensor is currently electrically coupled with the sensor interface; and one or more electronic couplers configured as a serial peripheral interface.

Example 2 is an apparatus in accordance with example 1, wherein the sensor interface further comprises a fourth electrical coupler configured to provide an electrical ground utilizable by electronics of the removable sensor. Example 3 is an apparatus in accordance with example 1, wherein the one or more electronic couplers comprise electronic couplers configured to transmit signals corresponding to a serial clock, sensor input data, sensor output data, and a select signal. Example 4 is an apparatus in accordance with example 1, wherein the removable sensor requires an initialization time interval to achieve an initialized state, and the continuous electrical power transmitted by the first electronic coupler maintains the removable sensor in the initialized state.

Example 5 is an apparatus in accordance with example 1, further comprising an electronic relay configured at least to cause electrical power to be provided to the second electronic coupler in response to a signal from the microcontroller. Example 6 is an apparatus in accordance with example 1, wherein, in response to the indication that the removable sensor is currently electrically coupled with the sensor interface, the microcontroller determines a type of the removable sensor. Example 7 is an apparatus in accordance with example 1, wherein the microcontroller utilizes the serial peripheral interface to send commands to the removable sensor. Example 8 is an apparatus in accordance with example 1, wherein the removable sensor utilizes the serial peripheral interface to send sensor data to the microcontroller.

Example 9 is an apparatus in accordance with example 1, further comprising a plurality of sensor interfaces electrically coupled with the microcontroller, each sensor interface capable of electrically coupling with a different removable sensor, and each sensor interface independently transmitting an indication as to whether a corresponding removable sensor is currently electrically coupled with the sensor interface. Example 10 is an apparatus in accordance with example 1, further comprising an IO expander electrically coupled with a plurality of sensor interfaces and corresponding removable sensors. Example 11 is an apparatus in accordance with example 1, further comprising a data logging module electrically coupled with the microcontroller and configured at least to log sensor data to a non-volatile memory card.

Example 12 is an apparatus in accordance with example 1, further comprising: a wireless communication management module electrically coupled with the microcontroller; and a plurality of wireless communication modules electrically coupled with the wireless communication management module, wherein the wireless communication management module is configured at least to select among the plurality of wireless communication modules to optimize one or more of: network connectivity, cost efficiency, and power utilization efficiency. Example 13 is an apparatus in accordance with example 12, wherein the plurality of wireless communication modules include at least one of: a Bluetooth wireless communication module, a ZigBee wireless communication module, a GPRS wireless communication module, and a Wi-Fi wireless communication module.

Example 14 is an apparatus in accordance with example 1, wherein utilizing the serial peripheral interface to communicate with the removable sensor comprises: transmitting a command identifier to the removable sensor; receiving a plurality of data packets that contribute to a data package containing sensor data generated by the removable sensor; receiving a received check sum determined with respect to the data package; determining a calculated check sum based at least in part on the plurality of data packets; and detecting whether a transmission error occurred at least in part by comparing the received check sum with the calculated check sum.

Example 15 is an apparatus for air quality measurement, the apparatus comprising: an air quality sensor; a sensor microcontroller electrically coupled with the air quality sensor; a first sensor interface electrically coupled with the sensor microcontroller, the first sensor interface comprising: a first electronic coupler configured to transmit continuous electrical power to the air quality sensor; a second electronic coupler configured to transmit intermittent electrical power to the sensor microcontroller during time intervals corresponding to sensing intervals; a third electronic coupler configured to transmit an indication that the third electronic coupler is currently electrically coupled with a corresponding electronic coupler of a second sensor interface that is physically complementary with respect to the first sensor interface; and one or more electronic couplers configured as a serial peripheral interface.

Example 16 is an apparatus in accordance with example 15, wherein the second sensor interface is one of a plurality of sensor interfaces incorporated into a sensor management module that is configured at least to receive sensor data from a plurality of air quality sensors through corresponding sensor interfaces of the plurality of sensor interfaces. Example 17 is an apparatus in accordance with example 16, wherein utilizing the serial peripheral interface to communicate with the sensor management module comprises: receiving a command identifier from the sensor management module; determining an operation of the air quality sensor to perform based at least in part on the command identifier; performing the determined operation of the air quality sensor to generate sensor data; transmitting a plurality of data packets corresponding to the sensor data; determining a check sum based at least in part on the transmitted sensor data; and transmitting the check sum.

Example 18 is one or more computer-readable media collectively having thereon computer-executable instructions that configure one or more devices to collectively, at least: receive, with a first electronic coupler of a sensor interface, an indication that a removable sensor is currently electrically coupled with the sensor interface; transmit, with a second electronic coupler of the sensor interface, a continuous supply of electrical power to the removable sensor; transmit, with a third electronic coupler of the sensor interface, an intermittent supply of electrical power during time intervals corresponding to sensing intervals; send, with one or more electronic couplers of the sensor interface configured as a serial peripheral interface, a command to the removable sensor; and receive, with the one or more electronic couplers of the sensor interface, sensor data corresponding to the command.

Example 19 is one or more computer-readable media in accordance with example 18, wherein the computer-executable instructions further configure the one or more devices to determine, responsive to the indication, a type of the removable sensor. Example 20 is one or more computer-readable media in accordance with example 19, wherein the computer-executable instructions further configure the one or more devices to determine the command to send to the removable sensor based at least in part on the determined type of the removable sensor All references, including publications, patent applications, and patents, cited herein are hereby incorporated by reference to the same extent as if each reference were individually and specifically indicated to be incorporated by reference and/or were set forth in its entirety herein.

The use of the terms "a" and "an" and "the" and similar referents in the specification and in the following claims are to be construed to cover both the singular and the plural, unless otherwise indicated herein or clearly contradicted by context. The terms "having," "including," "containing" and similar referents in the specification and in the following claims are to be construed as open-ended terms (e.g., meaning "including, but not limited to,") unless otherwise noted. Recitation of ranges of values herein are merely indented to serve as a shorthand method of referring individually to each separate value inclusively falling within the range, unless otherwise indicated herein, and each separate value is incorporated into the specification as if it were individually recited herein. All methods described herein can be performed in any suitable order unless otherwise indicated herein or clearly contradicted by context. The use of any and all examples, or exemplary language (e.g., "such as") provided herein, is intended merely to better illuminate embodiments of the invention and does not pose a limitation to the scope of the invention unless otherwise claimed. No language in the specification should be construed as indicating any non-claimed element as essential to each embodiment of the present invention.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. An apparatus for acquiring air quality data from one or more removable or replaceable sensors, processing and storing the acquired air quality data, and transmitting the processed and stored air quality data to a backend server, the apparatus comprising:
   a circuit board;
   a microcontroller electrically coupled with the circuit board;
   a removable or replaceable sensor; and
   a first standardized sensor interface electrically coupled with the circuit board and the microcontroller, the first standardized sensor interface comprising:

a first physical electronic coupler configured to transmit a continuous electrical power to the removable or replaceable sensor;

a second physical electronic coupler configured to transmit an intermittent electrical power to the removable or replaceable sensor during time intervals corresponding to sensing intervals determined by the microcontroller;

a third physical electronic coupler configured to transmit an indication to the microcontroller that the removable or replaceable sensor is currently electrically coupled with the first sensor interface;

a fourth physical electronic coupler configured to provide an electrical ground utilizable by electronics of the removable or replaceable sensor; and one or more additional physical electronic couplers configured as a serial peripheral interface, wherein the removable or replaceable sensor comprises physical electronic couplers that correspond to the physical electronic couplers of the first standardized sensor interface.

2. An apparatus in accordance with claim 1, wherein the one or more physical electronic couplers comprise electronic couplers configured to transmit and receive signals corresponding to a serial clock, sensor input data, sensor output data, and a select signal.

3. An apparatus in accordance with claim 1, wherein the removable or replaceable sensor requires an initialization time interval to achieve an initialized state, and the continuous electrical power transmitted by the first physical electronic coupler maintains the removable or replaceable sensor in the initialized state.

4. An apparatus in accordance with claim 1, further comprising an electronic relay configured at least to cause electrical power to be provided to the second physical electronic coupler in response to an electronic signal from the microcontroller.

5. An apparatus in accordance with claim 1, wherein, in response to the indication that the removable or replaceable sensor is currently electrically coupled with the first standardized sensor interface, the microcontroller determines a type of the removable or replaceable sensor.

6. An apparatus in accordance with claim 1, wherein the microcontroller utilizes the serial peripheral interface to send commands to and receive sensor data from the removable or replaceable sensor.

7. An apparatus in accordance with claim 1, wherein the removable or replaceable sensor utilizes the serial peripheral interface to receive commands from and send sensor data to the microcontroller.

8. An apparatus in accordance with claim 1, further comprising a plurality of standardized sensor interfaces incorporated into a sensor management module electrically coupled with the circuit board and the microcontroller, each standardized sensor interface comprising physical electronic couplers corresponding to the physical electronic couplers of the first standardized sensor interface, and each standardized sensor interface capable of electrically coupling with a different removable or replaceable sensor having corresponding physical electronic couplers.

9. An apparatus in accordance with claim 8, wherein the sensor management module comprises one or more input and output (IO) expanders electrically coupled with the circuit board and the microcontroller and expanding the first standardized sensor interface to a plurality of independently functional standardized sensor interfaces.

10. An apparatus in accordance with claim 9, wherein the one or more IO expanders comprise IO expanders configured to expand signals corresponding to, at least:

a control signal from the microcontroller via an electronic relay to cause electrical power to be provided to the second physical electronic coupler of a corresponding standardized sensor interface;

an indication signal to the microcontroller indicating whether a removable or replaceable sensor is currently electrically coupled with a corresponding standardized sensor interface; and a select signal from the microcontroller to initiate serial peripheral interface communication between the microcontroller and the removable or replaceable sensor coupled with a corresponding standardized sensor interface.

11. An apparatus in accordance with claim 1, further comprising a real-time clock module electrically coupled with the circuit board and the microcontroller and configured at least to provide date and time information.

12. An apparatus in accordance with claim 1, further comprising a global positioning system module electrically coupled with the circuit board and the microcontroller and configured at least to provide a current geographic location information.

13. An apparatus in accordance with claim 1, further comprising a data logging module electrically coupled with the circuit board and the microcontroller and configured at least to log sensor data, date and time information, and geographic location information to a non-volatile memory card.

14. An apparatus in accordance with claim 1, wherein utilizing the serial peripheral interface to communicate with the removable or replaceable sensor comprises:

transmitting a command identifier to the removable or replaceable sensor;

receiving a plurality of data packets that contribute to a data package containing sensor data generated by the removable or replaceable sensor;

receiving a received check sum determined with respect to the data package;

determining a calculated check sum based at least in part on the plurality of data packets; and detecting whether a transmission error occurred at least in part by comparing the received check sum with the calculated check sum.

15. An apparatus in accordance with claim 1, the removable or replaceable sensor comprising:

a sensor circuit board;

an air quality sensor;

a sensor microcontroller electrically coupled with the sensor circuit board and the air quality sensor; and a second standardized sensor interface electrically coupled with the sensor circuit board and the sensor microcontroller, the second standardized sensor interface comprising:

a fifth physical electronic coupler configured to transmit a continuous electrical power to the air quality sensor;

a sixth physical electronic coupler configured to transmit an intermittent electrical power to the sensor microcontroller during time intervals corresponding to sensing intervals;

a seventh physical electronic coupler configured to transmit an indication that the seventh physical electronic coupler is currently electrically coupled with a corresponding physical electronic coupler of the first standardized sensor interface that is physically complementary with respect to the second standardized sensor interface;

an eighth physical electrical coupler configured to provide an electrical ground utilizable by the air quality sensor and the sensor microcontroller; and one or more additional electronic couplers configured as a serial peripheral interface.

16. An apparatus in accordance with claim 15, wherein the first standardized sensor interface is one of a plurality of standardized sensor interfaces of a sensor management module that is configured at least to transmit commands and receive sensor data from a plurality of air quality sensors through corresponding standardized sensor interfaces of the sensor management module.

17. An apparatus in accordance with claim 16, wherein the removable or replaceable sensor utilizes the serial peripheral interface of the second standardized sensor interface to communicate with the sensor management module, the communication comprising:

receiving a command identifier from the sensor management module;

determining an operation of the air quality sensor to perform based at least in part on the command identifier;

performing the determined operation of the air quality sensor to generate sensor data;

transmitting a plurality of data packets corresponding to the sensor data;

determining a check sum based at least in part on the transmitted sensor data; and transmitting the check sum.

18. One or more computer-readable media collectively having thereon computer-executable instructions that configure one or more devices to collectively, at least:

transmit, with a first physical electronic coupler of a standardized sensor interface of a circuit board, a continuous supply of electrical power to a removable or replaceable sensor;

transmit, with a second physical electronic coupler of the standardized sensor interface, an intermittent supply of electrical power during time intervals corresponding to sensing intervals;

receive, with a third physical electronic coupler of the standardized sensor interface, an indication that the removable or replaceable sensor is currently electrically coupled with the standardized sensor interface;

send, with one or more physical electronic couplers of the standardized sensor interface configured as a serial peripheral interface, a command to the removable or replaceable sensor; and receive, with the one or more physical electronic couplers of the standardized sensor interface configured as a serial peripheral interface, sensor data corresponding to the command, wherein the removable or replaceable sensor comprises physical electronic couplers that correspond to the physical electronic couplers of the standardized sensor interface of the circuit board.

19. One or more computer-readable media in accordance with claim 18, wherein the computer-executable instructions further configure the one or more devices to determine, responsive to the indication, a type of the removable or replaceable sensor.

20. One or more computer-readable media in accordance with claim 19, wherein the computer-executable instructions further configure the one or more devices to determine the command to send to the removable or replaceable sensor based at least in part on the determined type of the removable or replaceable sensor.

21. An apparatus in accordance with claim 1, wherein the first standardized sensor interface comprises a universal sensor interface.

22. An apparatus in accordance with claim 15, wherein the first standardized sensor interface enables plug-and-play functionality with respect to removable or replaceable sensors having the second standardized sensor interface with physical electronic couplers that correspond to the physical electronic couplers of the first standardized sensor interface.

* * * * *